United States Patent
Isogai et al.

(10) Patent No.: US 9,550,977 B2
(45) Date of Patent: Jan. 24, 2017

(54) METHOD FOR PRODUCING AURICULAR CARTILAGE TISSUE

(71) Applicant: GUNZE LIMITED, Ayabe-shi, Kyoto (JP)

(72) Inventors: Noritaka Isogai, Osaka (JP); Yoshihito Itani, Osaka (JP); Akeo Hagiwara, Kyoto (JP); Shinichiro Morita, Kyoto (JP); Kosuke Sawai, Shiga (JP); Koichi Hatakeyama, Kyoto (JP)

(73) Assignee: GUNZE LIMITED, Kyoto (JP)

( * ) Notice: Subject to any disclaimer, the term of this patent is extended or adjusted under 35 U.S.C. 154(b) by 322 days.

(21) Appl. No.: 14/360,526

(22) PCT Filed: Nov. 30, 2012

(86) PCT No.: PCT/JP2012/081084
§ 371 (c)(1),
(2) Date: May 23, 2014

(87) PCT Pub. No.: WO2013/081103
PCT Pub. Date: Jun. 6, 2013

(65) Prior Publication Data
US 2014/0302606 A1  Oct. 9, 2014

(30) Foreign Application Priority Data

Dec. 2, 2011 (JP) .................................. 2011-264787

(51) Int. Cl.
| | | |
|---|---|---|
| *C12N 5/077* | (2010.01) | |
| *A61L 27/18* | (2006.01) | |
| *A61L 27/38* | (2006.01) | |

(52) U.S. Cl.
CPC ............. *C12N 5/0655* (2013.01); *A61L 27/18* (2013.01); *A61L 27/3817* (2013.01); *A61L 27/3852* (2013.01); *A61L 2430/06* (2013.01)

(58) Field of Classification Search
None
See application file for complete search history.

(56) References Cited

U.S. PATENT DOCUMENTS

| 2010/0049250 A1 | 2/2010 | Matsuda et al. |
| 2011/0038911 A1 | 2/2011 | Sakamoto et al. |

FOREIGN PATENT DOCUMENTS

| CN | 101563037 | 10/2009 |
| EP | 1 214 952 | 6/2002 |
| JP | 2001-078750 | 3/2001 |
| JP | 2003-193328 | 7/2003 |
| JP | 2003-204807 | 7/2003 |
| JP | 2007-236450 | 9/2007 |
| JP | 2008-245844 | 10/2008 |
| JP | 2011-509786 | 3/2011 |
| JP | 2003-019196 | 1/2013 |
| WO | 2009/019995 | 2/2009 |
| WO | 2009/093023 | 7/2009 |

OTHER PUBLICATIONS

Kusuhara, et al., "Tissue engineering a model for the human ear: Assessment of size, shape, morphology, and gene expression following seeding of different chondrocytes", Wound Repair and Regeneration, 2009, vol. 17, No. 1, pp. 136-146.

Terada, et al., "Saibo ni yoru Sanjigen Baiyo Jikai Nankotsu Sakusei no Kokoromi" (Experimental Study of Three-dimensional Tissue Engineered Auricular Cartilage), Keisei Geka, vol. 47, No. 9, 2004, pp. 975-982—English abstract on p. 8.

*Primary Examiner* — Blaine Lankford
(74) *Attorney, Agent, or Firm* — Hamre, Schumann, Mueller & Larson, P.C.

(57) ABSTRACT

The present invention aims to provide a method for producing auricular cartilage tissue having a sufficient thickness and mechanical strength, and auricular cartilage tissue produced by the method for producing auricular cartilage tissue. The present invention provides a method for producing auricular cartilage tissue, including the steps of: seeding auricular chondrocytes onto a non-woven fabric consisting of a bioabsorbable material having an average fiber diameter of 0.90 to 7.00 μm; and forming a composite of the non-woven fabric seeded with the auricular chondrocytes and a mesh-like framework consisting of a non-bioabsorbable material, and shaping the composite.

4 Claims, 2 Drawing Sheets

METHOD FOR PRODUCING AURICULAR CARTILAGE TISSUE

TECHNICAL FIELD

The present invention relates to a method for producing auricular cartilage tissue having a sufficient thickness and mechanical strength, and auricular cartilage tissue produced by the method for producing auricular cartilage tissue.

BACKGROUND ART

Recent advancements in the cellular engineering technology have made it possible to culture various types of animal cells including human cells. In addition, the study of so-called regenerative medicine, which tries to reconstruct human tissue and organs using the cultured cells, has been rapidly advancing. In the regenerative medicine, the key is whether cells grow and differentiate so as to allow construction of three-dimensional, body tissue-like structures. Methods employed include, for example, one in which cells and growth factors are used, and one in which a support as a scaffold for the regeneration of tissue or organ is implanted into a patient. As an example of such a support, an implant scaffold consisting of a collagen single yarn is disclosed in Patent Literature 1.

In addition, Patent Literature 2 and Patent Literature 3 disclose a foam consisting of a bioabsorbable material, a cardiovascular tissue culture scaffold reinforced by the bioabsorbable material, and a nerve regeneration scaffold having a tubular shape.

Further, Patent Literature 4 discloses a biomedical material including a gel having cells dispersed in a skeleton consisting of a sponge-like or non-woven polymeric molded material.

One of the subjects of the regenerative medicine is the regeneration of auricular cartilage tissue. Regeneration of auricular cartilage tissue requires large and thick tissue having a relatively high mechanical strength. Unfortunately, it has been difficult to produce such a large and thick auricular cartilage tissue by a method that uses a conventional scaffold to produce body tissue.

CITATION LIST

Patent Literature

Patent Literature 1: Japanese Kokai Publication No. 2003-193328 (JP-A 2003-193328)
Patent Literature 2: Japanese Kokai Publication No. 2001-78750 (JP-A 2001-78750)
Patent Literature 3: Japanese Kokai Publication No. 2003-19196 (JP-A 2003-19196)
Patent Literature 4: Japanese Kokai Publication No. 2003-204807 (JP-A 2003-204807)

SUMMARY OF INVENTION

Technical Problem

The present invention aims to provide a method for producing auricular cartilage tissue having a sufficient thickness and mechanical strength; and auricular cartilage tissue produced by the method for producing auricular cartilage tissue.

Solution to Problem

The present invention relates to a method for producing auricular cartilage tissue; including the steps of: seeding auricular chondrocytes onto a non-woven fabric consisting of a bioabsorbable material having an average fiber diameter of 0.90 to 7.00 μm; and forming a composite of the non-woven fabric seeded with the auricular chondrocytes and a mesh-like framework consisting of a non-bioabsorbable material, and shaping the composite.

The present invention is described in detail below.

The present inventors attempted to regenerate auricular cartilage tissue by seeding auricular chondrocytes onto supports formed from various materials and having various shapes, and as a result, they found that the regeneration of auricular cartilage tissue was remarkably promoted when a non-woven fabric consisting of a bioabsorbable material having an average fiber diameter of 0.90 to 7.00 μm was used, compared to when supports formed from other materials and having other shapes were used. As a result of further studies, the present inventors found that auricular cartilage tissue having a sufficient thickness and mechanical strength can be produced in the following manner: seeding auricular chondrocytes onto a non-woven fabric consisting of a bioabsorbable material having an average fiber diameter of 0.90 to 7.00 μm; and subsequently forming a composite of the above non-woven fabric and a mesh-like framework consisting of a non-bioabsorbable material, and shaping the composite. The present invention was accomplished based on these findings.

It is unclear why the regeneration of auricular cartilage tissue is particularly promoted by the use of a non-woven fabric consisting of a bioabsorbable material having an average fiber diameter of 0.90 to 7.00 μm. As an experiment, the present inventors seeded auricular chondrocytes onto multiple non-woven fabrics consisting of polyglycolide having different average fiber diameters, and counted the number of cells attached. The results showed that no significant increase in cell attachment was achieved by the use of a non-woven fabric having an average fiber diameter of 0.90 to 7.00 μm.

The method for producing auricular cartilage tissue of the present invention includes the step of seeding auricular chondrocytes onto a non-woven fabric consisting of a bioabsorbable material having an average fiber diameter of 0.90 to 7.00 μm (hereinafter also sometimes simply referred to as "non-woven fabric"). Auricular cartilage tissue having a sufficient thickness and mechanical strength is produced by the use of a non-woven fabric having such a specific average fiber diameter and consisting of such a specific material.

The bioabsorbable material is not particularly limited. Examples thereof include polyglycolide, polylactides (D-, L-, DL-isomer), polycaprolactone, glycolic acid-lactide (D-, L-, DL-isomer) copolymers, glycolic acid-ε-caprolactone copolymers, lactide (D-, L-, DL-isomer)-ε-caprolactone copolymers, and poly(p-dioxanone). These may be used alone or in combination of two or more thereof. Among these, polyglycolide or lactide (D-, L-, DL-isomer)-ε-caprolactone copolymers are preferred, and polyglycolide is more preferred.

The non-woven fabric has an average fiber diameter of 0.90 to 7.00 μm. The non-woven fabric having an average fiber diameter in the above range promotes the regeneration of auricular cartilage tissue. More specifically, the non-woven fabric having an average fiber diameter of 0.90 μm particularly promotes the regeneration of auricular cartilage tissue.

As for the average fiber diameter of the non-woven fabric as mentioned herein, a portion of the center of the non-woven fabric is cut out and observed under an electron microscope, and fibers in focus are randomly selected. Then, the diameters of the fibers in various portions of the fabric are measured until the total number of the fibers measured is at least 100. The average fiber diameter refers to an average value of the measured diameters of the at least 100 fibers.

A preferred lower limit of the fiber areal weight of the non-woven fabric is 1 g/m², and a preferred upper limit thereof is 100 g/m². If the fiber areal weight is outside of the above range, the regeneration of auricular cartilage tissue may be insufficient. A more preferred lower limit of the fiber areal weight of the non-woven fabric is 5 g/m², and a more preferred upper limit thereof is 50 g/m².

Any method can be used without limitation to produce the non-woven fabric consisting of a bioabsorbable material having an average fiber diameter of 0.90 to 7.00 μm. Examples of methods include conventionally known methods such as electro-spinning deposition, melt blowing, needle punching, spun-bonding, flash spinning, spun-lacing, airlaid, thermal bonding, resin bonding, and wet method. Among these, melt blowing is suitable.

In the step of seeding, auricular chondrocytes are seeded onto the non-woven fabric.

The auricular chondrocytes can be extracted by a conventionally known method. For example, auricular chondrocytes can be isolated in the following manner: removing the skin, connective tissue, and cartilage membranes from an auricle of a human or animal; cutting the auricle into small pieces (about 5 mm×5 mm in size); and treating the pieces with collagenase. The isolated auricular chondrocytes may be used as-is in the method for producing auricular cartilage tissue of the present invention, or may be grown in culture first and then used in the method for producing auricular cartilage tissue of the present invention.

The method for seeding is not particularly limited, and conventionally known seeding methods can be used.

The cell seeding density during seeding is not particularly limited. A preferred lower limit is $2.0 \times 10^7$ cells/cm², and a preferred upper limit is $1.0 \times 10^8$ cells/cm². If the cell seeding density is less than $2.0 \times 10^7$ cells/cm², it may take time until auricular cartilage tissue having a sufficient thickness and mechanical strength is formed, whereas the effect no longer increases after the cell seeding density exceeds $1.0 \times 10^8$ cells/cm². A more preferred lower limit of the cell seeding density is $5.0 \times 10^7$ cells/cm².

The non-woven fabric seeded with the auricular chondrocytes is preferably allowed to stand for about 10 minutes until the auricular chondrocytes are sufficiently attached to the non-woven fabric. In addition, if necessary, the auricular chondrocytes may be cultured for about several hours to several days. As a culture medium for culturing the auricular chondrocytes, for example, a serum-supplemented medium obtained by adding about 1 to 10% by weight of fetal bovine serum to a commonly used culture medium such as MEM or DMEM can be used.

The method for producing auricular cartilage tissue of the present invention includes the step of forming a composite of the non-woven fabric seeded with the auricular chondrocytes and a mesh-like framework consisting of a non-bioabsorbable material, and shaping the composite.

The regeneration of auricular cartilage tissue requires the formation of large and thick tissue. Shaping the tissue into the shape of the site of implantation is also important. The mesh-like framework consisting of a non-bioabsorbable material plays a role of adjusting the shape and thickness of the prepared auricular cartilage tissue to a desired shape and a desired thickness.

The non-bioabsorbable material forming the mesh-like framework is not particularly limited as long as it is non-toxic to the living body and has an adequate hardness and elasticity. Preferred examples include polypropylene, polyethylene, polytetrafluoroethylene (PTEF), and nylon.

The mesh-like framework preferably has a shape that corresponds to the target auricular cartilage tissue to be regenerated. For example, in the case where the entire auricle should be regenerated, the mesh-like framework preferably has a shape that corresponds to the entire auricle. Alternatively, the entire auricle may be divided into several parts, and several mesh-like frameworks each having a shape that corresponds to each part of the auricle may be formed and then combined to form the entire auricle.

The method for forming a composite of the non-woven fabric seeded with the auricular chondrocytes and the mesh-like framework is not particularly limited. The non-woven fabric may be sandwiched between two mesh-like frameworks and the resulting composite may be shaped into a desired shape, or the non-woven fabric seeded with the auricular chondrocytes may be wound around the mesh-like framework having a desired shape in such a manner that the mesh-like framework is wrapped with the non-woven fabric.

The auricular cartilage tissue produced by the method for producing auricular cartilage tissue of the present invention is implanted into the living body, whereby auricular cartilage tissue having a sufficient thickness and mechanical strength is regenerated.

In another aspect, the present invention also provides auricular cartilage tissue including: a non-woven fabric consisting of a bioabsorbable material having an average fiber diameter of 0.90 to 7.00 μm and seeded with auricular chondrocytes; and a mesh-like framework consisting of a non-bioabsorbable material.

Advantageous Effects of Invention

The present invention provides a method for producing auricular cartilage tissue having a sufficient thickness and mechanical strength, and auricular cartilage tissue produced by the method for producing auricular cartilage tissue.

DESCRIPTION OF EMBODIMENTS

The embodiment of the present invention is described in further detail with reference to the example below. However, the present invention is not limited to the example.

EXPERIMENTAL EXAMPLE (1) Preparation of a Non-Woven Fabric

A non-woven fabric obtained by melt blowing was stretched, or a tubular knitted fabric made by spinning was needle-punched into a non-woven fabric so as to obtain non-woven fabrics (thickness: 0.13 to 0.30 mm) consisting of polyglycolide having an average fiber diameter of 0.67 μm (sample I), 0.90 μm (sample II), 3.10 μm (sample III), 7.00 μm (sample IV), and 20.60 μm (sample V).

Figure 1:
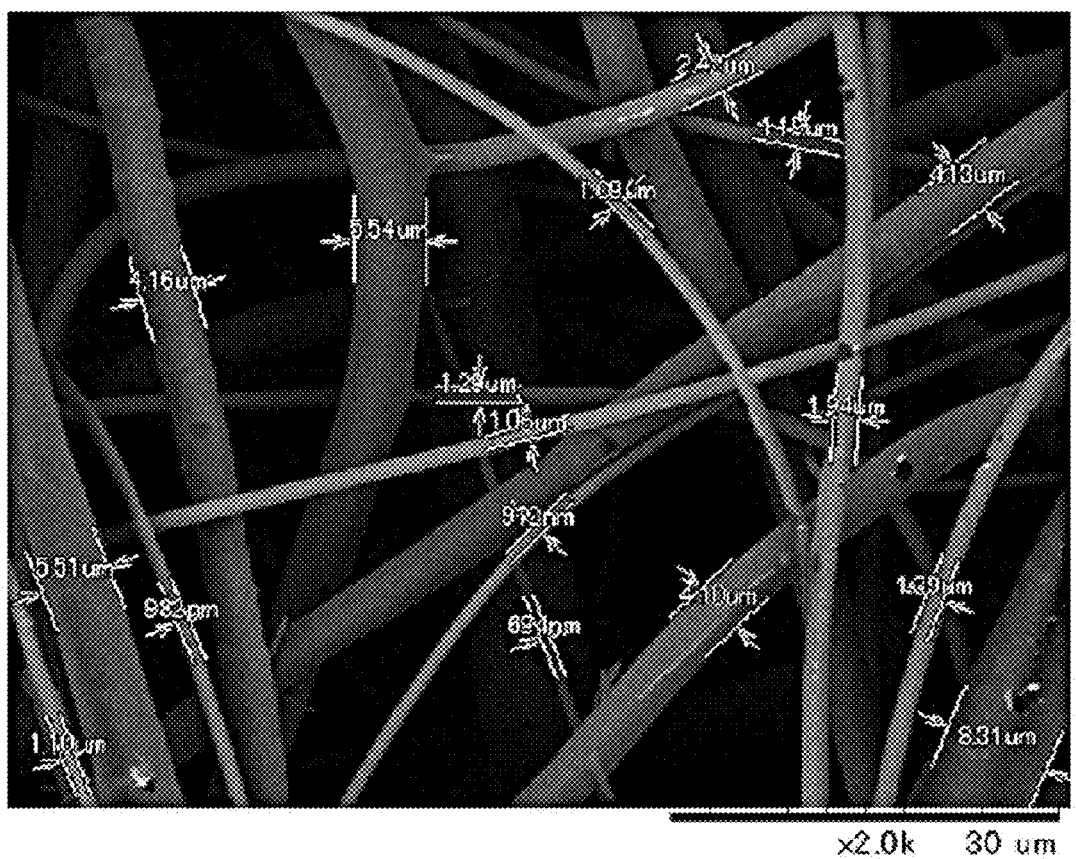
FIG. 1 is an electron micrograph showing a center portion of a non-woven fabric of sample III, prepared in an experimental example.
Figure 2:
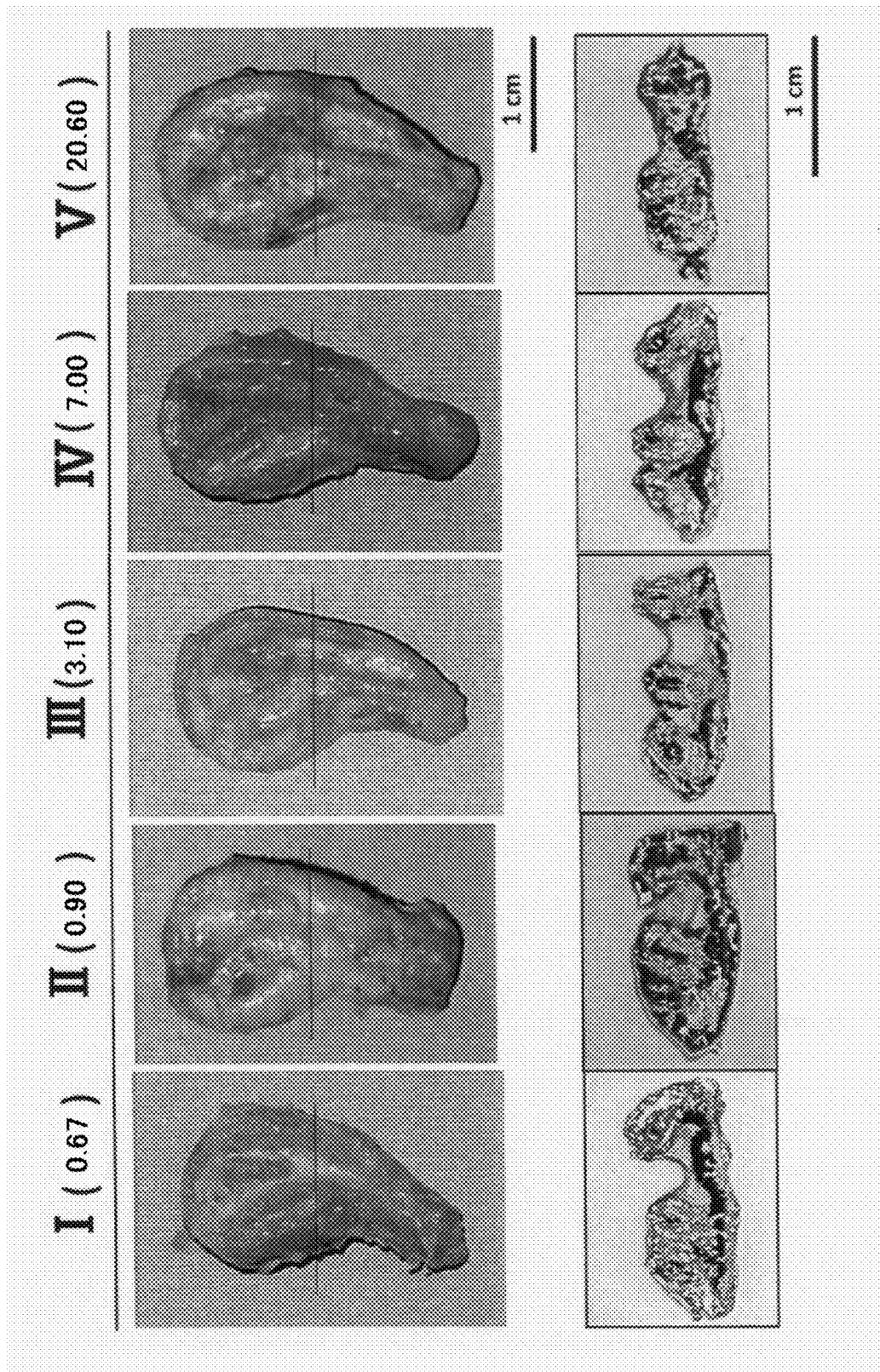
FIG. 2 is an image showing tissue sections of samples for confirming the regeneration of tissue five weeks after implantation.

A portion of the center of the non-woven fabric of sample III was cut out and observed under an electron microscope. FIG. 1 shows an electron micrograph of the portion (the bar below the electron micrograph represents 30 µm).

As shown in FIG. 1, fibers in focus in the electron micrograph were randomly selected, and the diameter of each fiber was measured. The diameters of the fibers in various portions of the fabric were measured until the total number of the fibers measured was 100, and the measured diameters of the 100 fibers were averaged. The average fiber diameter was determined to be 3.10 µm. The average fiber diameters of other samples I, II, IV, and V were also determined in the same manner.

(2) Isolation and Seeding of Auricular Chondrocytes

The left and right auricles of beagles (female, 6 to 8 weeks of age) were cut under anesthesia. The skin, connective tissue, and cartilage membranes were removed from the obtained auricles, and the auricles were cut into small pieces (about 5 mm×5 mm in size). The obtained pieces were treated with a collagenase solution (concentration: 0.3%) overnight. Subsequently, auricular chondrocytes were isolated. The isolated auricular chondrocytes were suspended in a phosphoric acid buffer to obtain a cell suspension ($1.0 \times 10^8$ cells/mL).

(3) Composite of the Non-Woven Fabric and a Mesh-Like Framework

A sheet-like mesh (2 cm×2 cm in size and 0.34±0.007 mm in thickness) consisting of a polypropylene was provided.

As a sample for measuring the flexural strength, a flat plate-shaped scaffold was produced by sandwiching each non-woven fabric seeded with the auricular chondrocytes between two sheet-like meshes so as to form a composite.

Meanwhile, as a sample for confirming the retention of the three-dimensional shape, a human auricle-shaped scaffold was produced by shaping parts formed by sandwiching each non-woven fabric seeded with the auricular chondrocytes between the sheet-like meshes into the shape of an auricle.

(4) Implantation

The obtained flat plate-shaped scaffold and human auricle-shaped scaffold were autoimplanted into the same beagles (female, 6 to 8 weeks of age). Specifically, the dorsal region of neck was incised under a general anesthetic, and the scaffolds were implanted and fixed between fascia layers in the head. The beagles were sacrificed five weeks after the implantation, and the samples were retrieved.

(Evaluation)

(1) Measurement of the Flexural Strength

The retrieved sample for measuring the flexural strength was tested to measure the flexural strength using an autograph in accordance with the method of Roy et al. Specifically, the flexural strength was measured in the following manner: the gap between the grips was adjusted to 1 cm; the sample (20 mm×5 mm in size) was fixed on the base; and a perpendicular plate was lowered at a speed of 0.02 mm/sec.

Table 1 shows the results.

TABLE 1

| Sample | Average fiber diameter of the non-woven fabric (µm) | Flexural strength of the sample (N) |
|---|---|---|
| I | 0.67 | 0.07 |
| II | 0.90 | 0.73 |
| III | 3.10 | 0.18 |
| IV | 7.00 | 0.38 |
| V | 20.60 | 0.31 |

Table 1 shows that a relatively high flexural strength was resulted from the use of the non-woven fabrics having an average fiber diameter of 0.90 µm or more (sample II to V), whereas a remarkably poor flexural strength was resulted from the use of the non-woven fabric having an average fiber diameter of 0.67 µm (sample I).

(2) Evaluation of Auricular Cartilage Tissue Regeneration

FIG. 1 shows images of the appearance of the retrieved samples for confirming the retention of the three-dimensional shape, and images of stained cross sections. The samples were cut along the lines in the upper images in FIG. 1, and the cross sections of the samples were stained with safranin O.

FIG. 1 shows that the regeneration of cartilage was sufficiently induced by the use of the non-woven fabrics having an average fiber diameter of 0.90 µm or more (sample II to V), whereas the regeneration of cartilage was poorly induced by the use of the non-woven fabric having an average fiber diameter of 0.67 µm (sample I).

(Reference Experiment)

The same method as in the above experimental example was used to obtain non-woven fabrics (thickness: 0.13 to 0.30 mm) consisting of polyglycolide having an average fiber diameter of 0.67 µm (sample I), 0.90 µm (sample II), 3.10 µm (sample III), 7.00 µm (sample IV), and 20.60 µm (sample V).

The left and right auricles of beagles (female, 6 to 8 weeks of age) were cut under anesthesia. The skin, connective tissue, and cartilage membranes were removed from the obtained auricles, and the auricles were cut into small pieces (about 5 mm×5 mm in size). The obtained pieces were treated with a collagenase solution (concentration: 0.3%) overnight. Subsequently, auricular chondrocytes were isolated. The isolated auricular chondrocytes were suspended in a phosphoric acid buffer to obtain a cell suspension ($1.0 \times 10^8$ cells/mL).

The obtained cell suspension (200 µL) was seeded onto the non-woven fabrics that were cut into a size of 2 cm×2 cm.

After seeding, the non-woven fabrics were divided into two groups. Fibrin glue (a mixture of fibrinogen and thrombin) was sprayed onto one group.

The group was allowed to stand for five minutes after the fibrin glue was sprayed thereto. Then, both groups were immersed in a 2.5% glutaraldehyde solution to obtain samples.

Each non-woven fabric was cut into 100-µm pieces, and these pieces were stained with toluidine blue. Subsequently, the chondrocytes infiltrated in the non-woven fabrics were measured and the number of cells were counted.

Table 2 shows the results.

TABLE 2

| Sample | Average fiber diameter of the non-woven fabric (µm) | Cell density (cell/$10^4$ um$^2$) Fibrinogen glue sprayed | Cell density (cell/$10^4$ um$^2$) Fibrinogen glue not sprayed | Remarks |
|---|---|---|---|---|
| I | 0.67 | 0.3 | 0.4 | There are spaces between the fibers, and the cells are not sufficiently incorporated. |
| II | 0.90 | 4.6 | 4.2 | |
| III | 3.10 | 5.2 | 5.7 | |
| IV | 7.00 | 4.5 | 4.2 | |

TABLE 2-continued

| Sample | Average fiber diameter of the non-woven fabric (μm) | Cell density (cell/$10^4$ μm$^2$) Fibrinogen glue sprayed | Cell density (cell/$10^4$ μm$^2$) Fibrinogen glue not sprayed | Remarks |
|---|---|---|---|---|
| V | 20.60 | 2.5 | 1.2 | The cells are distributed only around fiber bundles, and the resulting in a non-uniform distribution. |

As shown in FIG. 1, in the case of the non-woven fabric having an average fiber diameter of 0.67 μm (sample I), the cell density was low with spaces between the fibers, and the cells were not sufficiently incorporated into the fabric. In the case of the non-woven fabric having an average fiber diameter of 20.60 μm (sample V), the cell density was low, and the cells were distributed only around fiber bundles, resulting in a non-uniform distribution. The non-woven fabrics having an average fiber diameter of 0.90 μm (sample II) to 7.00 μm (sample IV) achieved high cell densities.

According to the results of the flexural strength measurement shown in Table 1, the non-woven fabrics having an average fiber diameter of 0.90 μm or more (samples II to V) achieved relatively high strengths.

According to the results of the cell density shown in Table 2, the non-woven fabrics having an average fiber diameter of 0.90 μm (sample II) to 7.00 μm (sample IV) achieved good results.

This indicates that the non-woven fabrics having an average fiber diameter of 0.90 μm (sample II) to 7.00 μm (sample IV) used for the regeneration of cartilage tissue are the most suitable for the regeneration of auricular cartilage.

INDUSTRIAL APPLICABILITY

The present invention provides a method for producing auricular cartilage tissue having a sufficient thickness and mechanical strength, and auricular cartilage tissue produced by the method for producing auricular cartilage tissue.

The invention claimed is:

1. A method for producing auricular cartilage tissue, comprising steps of:
   seeding auricular chondrocytes onto a non-woven fabric consisting of a bioabsorbable material having an average fiber diameter of 0.90 to 7.00 μm; and
   forming a composite of the non-woven fabric seeded with the auricular chondrocytes and a mesh framework consisting of a non-bioabsorbable material; and
   shaping the composite.

2. The method for producing auricular cartilage tissue according to claim 1,
   wherein the non-woven fabric consisting of a bioabsorbable material has an average fiber diameter of 0.90 μm.

3. The method for producing auricular cartilage tissue according to claim 1,
   wherein the bioabsorbable material is polyglycolide or a lactide (D-, L-, DL-isomer)-ε-caprolactone copolymer.

4. Auricular cartilage tissue comprising:
   a non-woven fabric consisting of a bioabsorbable material having an average fiber diameter of 0.90 to 7.00 μm and seeded with auricular chondrocytes; and
   a mesh framework consisting of a non-bioabsorbable material.

* * * * *